United States Patent
Alshomer et al.

(10) Patent No.: US 11,617,585 B2
(45) Date of Patent: Apr. 4, 2023

(54) LOW-COST 3D-PRINTED TOOL WITH MULTIAXIAL/ANGULAR VESSEL ORIENTATION FOR MICROVASCULAR ANASTOMOSIS TRAINING

(71) Applicants: National Guard Health Affairs, Riyadh (SA); King Saud Bin Abdulaziz University for Health Sciences, Riyadh (SA); King Abdullah International Medical Research Center, Riyadh (SA)

(72) Inventors: Feras Alshomer, Riyadh (SA); Salah Aldekhayel, Riyadh (SA)

(73) Assignees: National Guard Health Affairs, Riyadh (SA); King Saud Bin Abdulaziz University for Health Sciences, Riyadh (SA); King Abdullah International Medical Research Center, Riyadh (SA)

( * ) Notice: Subject to any disclaimer, the term of this patent is extended or adjusted under 35 U.S.C. 154(b) by 281 days.

(21) Appl. No.: 16/893,045

(22) Filed: Jun. 4, 2020

(65) Prior Publication Data
US 2021/0378670 A1    Dec. 9, 2021

(51) Int. Cl.
| | | |
|---|---|---|
| *A61B 17/11* | (2006.01) | |
| *G09B 23/30* | (2006.01) | |
| *B33Y 80/00* | (2015.01) | |
| *B33Y 70/00* | (2020.01) | |
| *B29C 64/118* | (2017.01) | |
| *A61B 17/00* | (2006.01) | |
| *B33Y 10/00* | (2015.01) | |
| *B29K 75/00* | (2006.01) | |
| *B29L 31/40* | (2006.01) | |

(Continued)

(52) U.S. Cl.
CPC ............ *A61B 17/11* (2013.01); *B29C 64/118* (2017.08); *B33Y 70/00* (2014.12); *B33Y 80/00* (2014.12); *G09B 23/306* (2013.01); *A61B 2017/00526* (2013.01); *A61B 2017/00955* (2013.01); *A61B 2017/1107* (2013.01); *B29C 64/386* (2017.08); *B29K 2075/00* (2013.01); *B29L 2031/40* (2013.01); *B33Y 10/00* (2014.12); *B33Y 50/00* (2014.12)

(58) Field of Classification Search
None
See application file for complete search history.

(56) References Cited

U.S. PATENT DOCUMENTS 9,070,306 B2 *  6/2015  Rappel .................. G16H 20/40
9,336,692 B1     5/2016  Stoll (Continued)

FOREIGN PATENT DOCUMENTS

| CN | 209607187 U | 11/2019 | |
|---|---|---|---|
| EP | 3306594 B1 * | 1/2020 | ............ G09B 19/24 |

(Continued)

*Primary Examiner* — Mohammad M Ameen
(74) *Attorney, Agent, or Firm* — Oblon, McClelland, Maier & Neustadt, L.L.P.

(57) ABSTRACT

A ethically sound, safe, feasible, and cost-effective microsurgery practice technique that can easily be practiced by trainees having different skill levels and an adjustable device for holding and manipulating vascular tissue during microsurgery practice, especially for practicing anastomoses.

19 Claims, 19 Drawing Sheets

(51) Int. Cl.
*B33Y 50/00* (2015.01)
*B29C 64/386* (2017.01)

(56) References Cited

U.S. PATENT DOCUMENTS

| | | | |
|---|---|---|---|
| 2008/0061210 A1* | 3/2008 | Carnevali | A47B 23/043 |
| | | | 248/447 |
| 2009/0138025 A1* | 5/2009 | Stabler | A61B 34/71 |
| | | | 606/130 |
| 2012/0115117 A1* | 5/2012 | Marshall | G09B 23/28 |
| | | | 434/262 |
| 2012/0141965 A1* | 6/2012 | Nakamura | G09B 23/32 |
| | | | 434/262 |
| 2016/0247418 A1 | 8/2016 | Folzenlogen et al. | |
| 2017/0169733 A1* | 6/2017 | Peterson | B33Y 10/00 |
| 2019/0152133 A1* | 5/2019 | Busbee | B33Y 70/00 |

FOREIGN PATENT DOCUMENTS

| | | |
|---|---|---|
| JP | 2013-76945 | 4/2013 |
| WO | 2008/044649 A1 | 4/2008 |

\* cited by examiner

LOW-COST 3D-PRINTED TOOL WITH MULTIAXIAL/ANGULAR VESSEL ORIENTATION FOR MICROVASCULAR ANASTOMOSIS TRAINING

STATEMENT REGARDING PRIOR DISCLOSURES BY THE INVENTOR OR A JOINT INVENTOR

Related technology was described in *Plast Reconstr Surg Glob Open* 2020; 8:*e*2567; doi: 10.1097/GOX.0000000000002567; Published online 11 Feb. 2020 and was disclosed at 10th Congress of World Society for Reconstructive Microsurgery, Bologna, Italy (Jul. 1, 2019).

BACKGROUND OF THE INVENTION

Field of the Invention

Microsurgery is one of the most complex surgical disciplines. It requires a delicate touch and a high level of hand dexterity to obtain a successful surgical outcome. Performing microsurgery on living animal models as practice for clinical procedures on human is considered the gold standard. However, there is a need for more ethically sound, safe, feasible, and cost-effective microsurgery practice techniques that can easily be practiced by trainees having different skill levels; Evgeniou E, et al. *The role of simulation in microsurgical training*. J Surg Educ. 2018; 75:171-181.

Various synthetic training tools, not requiring training on living animals have been described. These tools permit medical personnel to acquire basic microsurgical techniques as well as for skilled surgeons to maintain surgical dexterity during periods of inactivity; Evgeniou et al., supra. Studies have shown that simulated training on low-fidelity models is effective for establishing microsurgical skills that can be later transferred to animal or cadaveric models; Ghanem A M, et al. *A systematic review of evidence for education and training interventions in microsurgery*. Arch Plast Surg. 2013; 40:312-319. An improved technical performance in a simulated training model can translate to significant reductions in the numbers of hours needed for microsurgical practice on animals and in the associated costs; Singh M, et al. *Development of a five-day basic microsurgery simulation training course: a cost analysis*. Arch Plast Surg. 2014; 41:213-217.

Nonliving training models that mimic microvascular anastomosis and nerve repair have been described. These models include those using various tubes to simulate vascular structures including GORE-TEX® tubes, polyurethane tubes such as those found in intravenous cannula, rubber tubes, and premade practice cards having silicone microtubes affixed to them; Evgeniou et al., supra; Singh et al., supra; and Matsumura N, et al. *Basic training model for supermicrosurgery: a novel practice card model*. J Reconstr Microsurg. 2011; 27:377-382. However, each of these modalities fails to adequately model complex clinical microsurgical procedures because they lack the natural three-dimensionality of complex clinical microsurgical procedures. These models fall short of adequately training surgeons for performing clinical procedures like anastomosis under conditions were vessels are positioned in unique three dimensional positions or are only accessible at a particular angle.

In view of the many problems and limitations of microsurgical techniques requiring live animals and existing simulation models, the inventors sought to develop new tools and microsurgical training methods that more accurately model actual clinical microsurgical procedures in three dimensions and that are ethically sound and avoid the high costs and other problems associated with animal models.

BRIEF SUMMARY OF THE INVENTION

This technology involves a device for practicing anastomosis of two or more vessels, to training methods using this device, and to methods for easily and cheaply producing the device by 3D printing. Embodiments of this technology include, but are not limited to, the following.

One aspect of this technology is directed to a device comprising an upper and lower unit, wherein the upper unit comprises a flat circular platform and two clamps, wherein the two clamps are on opposite sides of the circular platform, wherein each of the clamps is configured to hold a peripheral end of a vessel and position the medial ends of the vessels in proximity so as to permit anastomosis of the medial ends, and wherein the upper unit further comprises a ball portion of a ball-in-socket joint; wherein the lower unit comprises a base and a socket portion of a ball-in-socket joint; wherein the upper and lower units are joined by connection of the ball portion of the upper unit and the socket portion of the lower unit, see FIGS. 1A-1C and 1G. In some embodiments the working surface 120 is inset into the circular platform. In other embodiments, it may be flush with the platform surface to which the clamps are attached.

Typically the upper and lower units are 3D printed, for example, with a material or ink comprising thermoplastic polyurethane, such as thermoplastic polyurethane measuring 95A on the Shore durometer (scale A) or having the other properties of ULTIMAKER® TPU 95A semiflexible filament. ULTIMAKER® TPU 95A (thermoplastic polyurethane) filament is a member of the ULTIMAKER® family of filaments. TPU 95A is semi-flexible, measuring 95A on the Shore durometer and is capable of withstanding up to 580% elongation at break. TPU 95A possesses high impact strength, is highly resistant to wear and tear, and is also resistant to many industrial oils and chemicals. Other thermoplastic polyurethanes or 3D printing materials having a hardness of at least 70, 75, 80, 85, 90 or 95 as measured on a Shore durometer may also be selected.

In this device, the clamps on the top surface of the platform of the upper unit may be 3D printed and integral to the platform or the clamps may be independently attached to the top surface with pegs, pins, adhesives or by other means known in the art.

In some embodiments of this device, the ball portion of the upper unit comprises a threaded cap and the socket portion of the lower unit comprises external threads compatible with those on the threaded cap, wherein the cap fits over the ball portion and secures it to the socket. The cap when engaged to the external threads of the socket secures the ball-in-socket joint in a fixed position, for example, in a locked vertical position, see threaded cap shown in FIG. 9.

In some embodiments, the ball has ridges or indentations on its surface complementary to counter ridges or counter indentations on the inner surface of the socket. These permit interactions between the surfaces of the ball and the socket while the device is being manipulated and help control or stabilize the tilt and rotation angles of the platform. In some embodiments, the ridges or indentations, or counter ridges and indentations, may range in width from <0.5, 0.5, 0.75, 1.0, 1.25, 1.5 to >1.5 mm and in height/depth from 2, 3, 4, 5, 6 or >6 mm.

In another embodiment the socket portion comprises an elastic material which permits the socket portion to stretch and control the motion of the attached ball.

In some embodiments, the platform further comprises protractor markings around its 360 degree circumference and the base comprises a groove or mark for use as a reference point. Markings may be made at intervals of choice, for example, at 5, 10, 20, 30, 40, 50, 60 or 120 degree increments or at any other interval of choice; see FIG. 10.

In other embodiments, to measure a degree of tilt in the X or Y directions of the planar platform, the ball portion of the upper unit is marked with protractor markings indicating a degree of tilt between 0, 5, 10, 15, 20, 25 and 30 degrees (or any intermediate value) along the X, Y or both X and Y axes. The protractor markings may be made on four sides of the ball spaced 90 degrees apart or may be indicated by concentric markings on the surface of the ball so that when the position of the ball changes the new tilt is indicated. Typically, the markings are visible on the portion of the ball not inside of the socket or through vertical gaps in the socket which may be spaced at the same intervals as the markings, for example, the gaps or windows 102 in the socket 104 may occur at 90 degree intervals; see FIG. 11 which describes on embodiment of these protractor markings.

In other embodiments, to measure tilt, the platform further comprises an inclinometer or tilt indicator that measures tilt in the X and/or Y directions.

In some embodiments, the upper surface of the platform is textured, gridded, embossed, or imprinted with a pattern or coated to permit seating of the tissue on the working surface 120; the surface may also be fenestrated to permit drainage of fluids, see FIGS. 1D-1F. In other embodiments, the surface 120 may be coated with a repellant material to prevent adhesion between blood and other biological fluid or tissues to make work on the surface easier. Area 120 may have fenestrations in its base that allow escape of fluids from its surface. Additionally, area 120 can be configured to receive a background sheet or inert, for example, a sheet having a contrasting color or texture with vessels placed on the surface and which acts as a background or as an absorbing surface.

Another aspect of this technology is a method for training a subject to perform anastomosis comprising: securing a peripheral end of a blood vessel under each clamp so that the medial ends of the blood vessels extend toward each other near the center of the circular platform, rotating the platform to a predetermined angle between 0 and 360 degrees with respect to the subject, tilting the platform to predetermined angles between 0 and 30 degrees with respect to tilt along the X and Y axes of the platform independent from the degree of platform rotation, and surgically manipulating or suturing the ends of the blood vessels to form an anastomosis between them. Tilting of the platform and workspace 120 is shown by FIGS. 8A-8C.

Sequential illustrations of a training procedure are shown by FIGS. 2A-2F. A workstation for training including a binocular microscope is shown by FIGS. 3A and 3B.

Any subject in need of training, maintaining skill levels, or learning new anastomosis procedures may use the device, for example, medical or nursing students, nurses, nurse practitioners, veterinarians, or doctors. In some alternative embodiments, the device may be used to practice other surgical techniques that require three dimensional orientation or angulation of a tissue.

In some embodiments, the vessels manipulated or anastomosed during training are obtained from an animal. In other embodiments, the vessels are obtained from a human cadaver and in other embodiments, the vessels are synthetic. In some embodiments, the training comprises suturing and or gluing ends of the vessels together.

Another aspect of this technology is directed to a method for 3D printing the training device as disclosed herein comprising selecting design parameters for the upper and lower units of the device including the shape, texture, size and thickness of the platform, the size of the ball and socket elements, the position of the clamps, and the shape and size of the base, incorporating the design into stereo-lithography file format, 3D printing the upper and lower units of the device using a 3D printer and the stereo-lithography file, removing excess material from the 3D printed upper and lower units, and when clamps are 3D printed excess material from the clamps, fitting the ball portion of the upper unit into the socket portion of the lower unit, thereby producing the training device. In some embodiments of this method the design parameters of the upper and lower units comprise a design for a threaded cap and externally threaded socket and wherein the cap may be independently 3D printed from the upper unit. The cap when engaged to the external threads of the socket can secure the ball-in-socket joint in a desired position or lock it in a vertical position. FIG. 9 shows an example of a threaded cap which can be used to tighten or lock the ball-in-socket joint.

In other embodiments, the outer surface of the ball may have ridges or indentations that help stabilize, hold, or lock a specific adjusted position of the overlying platform by friction or by interactions with counter ridges or counter indentations in or on the socket. In one embodiment, the ball invaginates so as to securely fit inside the socket portion. In preferred embodiments, the 3D printing is performed using material or ink comprising thermoplastic polyurethane. In some embodiments, the design of the platform of the upper unit comprises protractor markings around the circumference of the platform which are 3D printed into or on to the platform and the design of the base of the lower unit comprises a reference point marking which is printed into or onto the base. Any sequence of intervals between 0 and 360 degrees may be used, for example, intervals of 5, 10, 15, 20, 25, 30, 35, 40, 45, 50, 55, 60, 90 or 120 degrees; see FIG. 10.

In another embodiment, the design of the ball of the upper unit comprises protractor markings indicating a degree of tilt in the X and/or Y directions of 0, 5, 10, 15, 20, 25 to 30 degrees (or any sequence of markings between 0 and 30 degrees) which are 3D printed into or on to different sides of the ball with a spacing of 90 degrees.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Microsurgical anastomosis is a technically demanding skill requiring proper positioning and orientation of vascular tissue as well as surgical dexterity. Different microsurgical procedures involving vessels at different orientations or angles require different levels of training. A training device for securely holding vascular tissue and positioning it at different degrees of orientation and angulation is described herein. This device provides a safe, effective and affordable training model that can be used to practice a variety of different surgical procedures by trainees having different skill levels and which avoids the use of live animals.

The training device comprises an upper and lower unit which can each be separately 3D printed. The upper unit comprises a platform (tabletop) which has a shape and size suitable for securing vascular tissue. Preferably, the platform is circular, but in some embodiments or for specialized training procedures may be oval, rectangular, square or other shapes.

The upper unit comprises one or more clamps, typically two, attached to opposing sides of the platform of the upper unit. The clamps may be attached to the platform with pegs, pins, glue or other adhesive or alternatively can be 3D printed as an integral part of the platform. The bottom surface of the platform comprises one part of a ball-in-socket joint, either a ball or the socket. Preferably, the upper unit comprises a ball portion of a ball-in-socket joint. In some embodiments, the ball portion comprises a short rod which attaches it to the platform.

Figure 10:
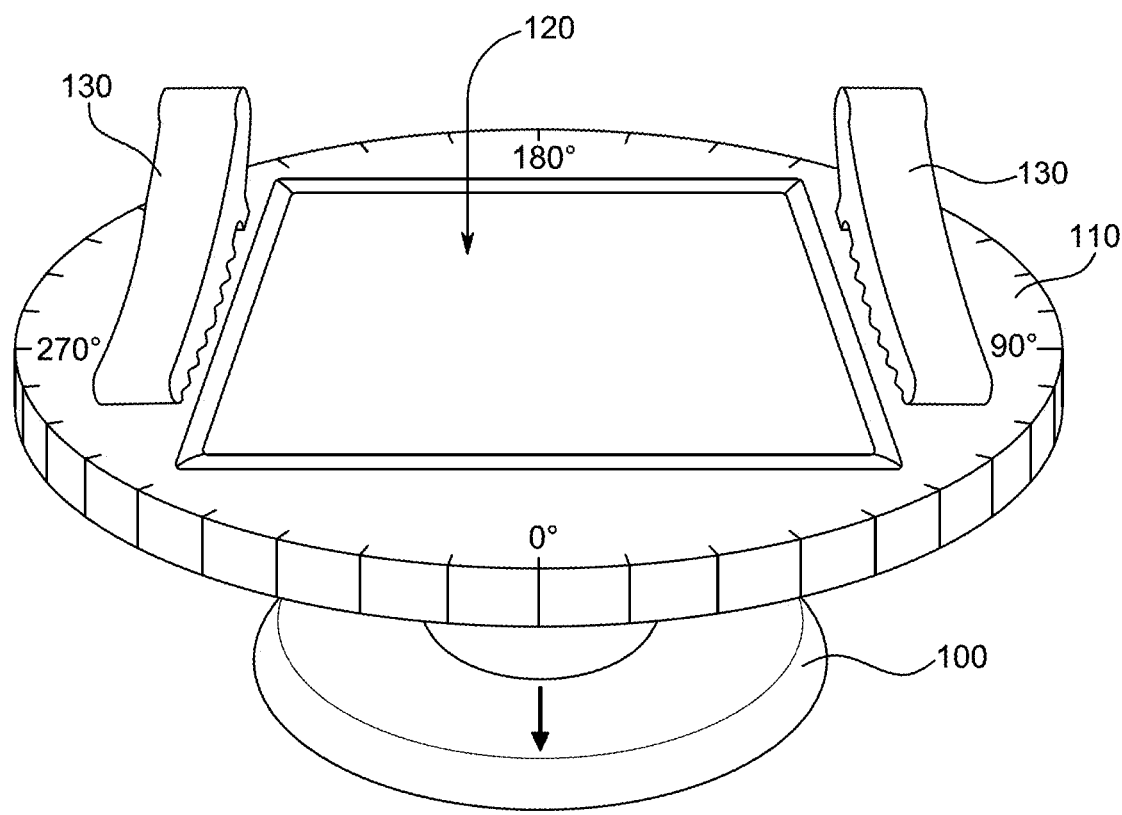
FIG. 10 depicts a stage having protractor markings and a base having a reference point for determining the degree of platform rotation. Typically the reference point faces the trainee using the device.
Figure 11:
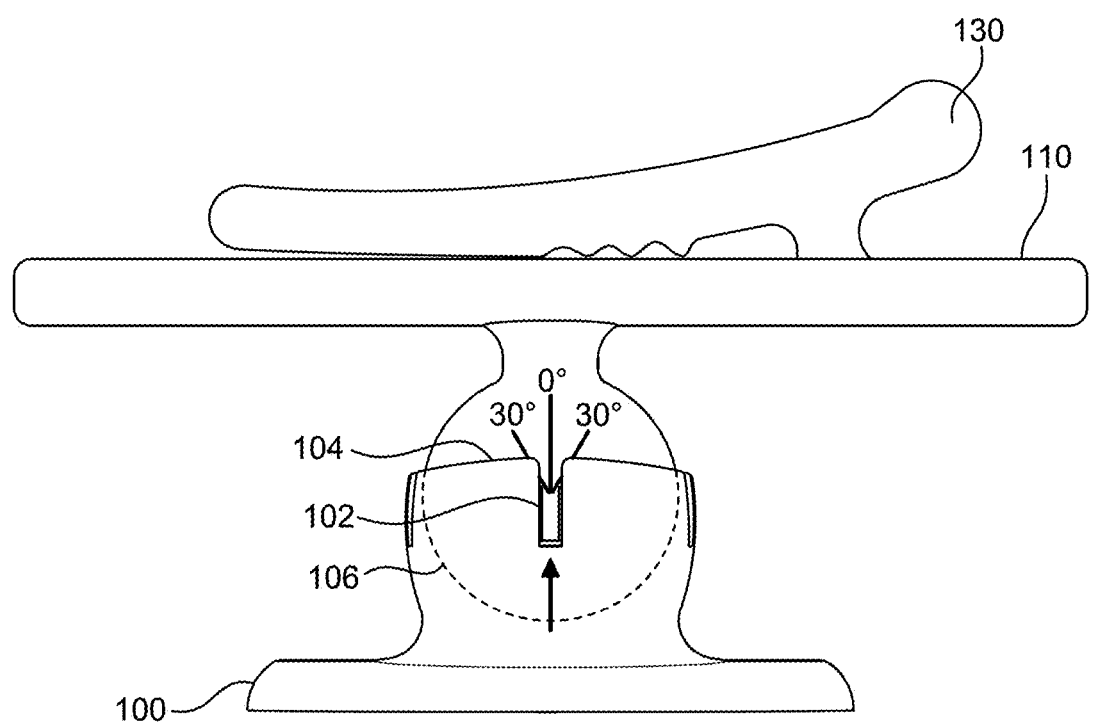
FIG. 11 depicts one embodiment of protractor markings on the ball portion of the upper unit. Tilt of the platform up to 30 degrees in the X or Y directions can be visualized using the markings on the ball which appear on each side of the ball spaced 90 degrees apart (other sides not shown). When the platform is parallel to the base (ground) the degree of tilt is zero in both the X and Y directions.

The platform can be 3D printed, imprinted, embossed or marked with protractor markings which indicate a degree of rotation with respect to a reference point, such as a mark or groove on the base of the device, see FIGS. 10 and 11. Suitable markings indicating the degree of rotation of the platform, such as markings every 5, 10, 15, 20, 25, 30, 35, 40, 45, 50, 55, 60, 90, 120 or 180 degrees, may be selected by a skilled surgeon or medical trainer. These markings assist the user in positioning vascular tissue or in recreating an angular position of the vascular tissue during anastomosis.

In other embodiments, the ball of the ball-in-socket joint can be 3D printed, imprinted, embossed or marked with protractor markings indicating the degree of forward or lateral tilt of the platform. Preferably, these markings will indicate a degree of tilt between 0, 5, 10, 15, 20, 25, 30, 35, 40 and 45 degrees, preferably from about 0 to 30 degrees in either, or both, the front to back or lateral (side-to-side) directions, see FIG. 10. These markings can be imposed on perpendicular surfaces of the ball so as to indicate tilt on both the X and Y axes assist the user in positioning vascular tissue or in recreating a particular degree of forward/backward or lateral tilt of the vascular tissue during anastomosis.

Alternatively, a degree of tilt may be indicated by concentric protractor markings applied to the surface of the ball in combination with a reference mark on the base.

In some embodiments, the platform may be operative connected to an inclinometer, tilt indicator, or pitch and role indicator which are instruments used for measuring angles of slope (or tilt), elevation, or depression of an object with respect to gravity's direction. A two axis inclinometer may be used which provides for simultaneous measurement of two-dimensional (X-Y plane) tilt angles (i.e. roll and pitch). These inclinometer devices permit a trainee to set and identify a particular positioning of the platform and return to it later in a subsequent training. Such devices are commercially available and are incorporated by reference to hyper text transfer protocol secure://en.wikipedia.org/wiki/Inclinometer (last accessed May 29, 2020).

A ball-in-socket joint connects the upper unit to a lower unit which comprises a base that provides a stable footing for the device when assembled. In one embodiment, a surface of the base is attached to an substrate, such as an operating surface or microscope platform, for example by a mechanical fastener or by an adhesive, such as with adhesive tape.

The ball-in-socket joint permits the platform to be rotated from 0 to 360 degrees so that vascular tissue may be viewed or accessed at different angles during anastomosis training. It also permits the platform to tilt in the X (side-to-side, roll) and/or Y (toward or away from trainee, pitch) directions.

As described above, the base may be printed, imprinted, or marked with a reference point.

The upper and lower units are typically independently 3D printed and then assembled.

Once assembled, vascular tissue or synthetic vascular tissue is clamped to the top surface of the platform. Typically, for anastomosis training, the distal ends of two detached segments of a vessel, or two different detached vessels, are secure under the clamps on each side of the platform with a small gap between the medial ends near the center of the platform. The medial ends of each vessel may overlap so as to facilitate anastomosis. Once secured to the platform, the medial ends of vessel are used to practice anastomosis.

Computer-aided design and 3D printing, such as desktop 3D printing, provides an affordable training device capable of providing trainees with different vessel orientation and angulation that can be used both with loupe magnification and under an operative microscope to mimic the complexity of different clinical scenarios especially those involving awkward angulations or orientations of vessels to be anastomosed.

A virtual model of the upper and lower units can be made using computer aided design, for example, a 2D model, 3D model, or CAD model. Preferably, the computer-aided design of the training device and its 3D printing comprise incorporating a design of the upper and/or lower units of the training device into stereo-lithography file format (STL). 3D-printing technology offers a new frontier in modern surgery and has myriad applications in medical education and surgical simulation; Hoang D, et al. *Surgical applications of three-dimensional printing: a review of the current literature & how to get started*. Ann Transl Med. 2016; 4:456 (incorporated by reference).

A 3D printer can use the stereolithography file to print the upper and lower units of the device using a suitable 3D printing material or ink. In one embodiment, a model was 3D printed with a thermoplastic polyurethane (TPU 95A) semiflexible filament on a desktop fused deposition modeling, Ultimaker® 2+3D printer. For this 3D-printing process, the average printing time was about 3 and a half hours with an average material cost of $1.30.

Once printed, the upper and lower units are cleaned from residual print support material. The upper and lower units are then assembled by fitting the ball on one unit into the socket on the other unit. Preferably, the upper unit comprises the ball portion of the joint and the lower unit comprises the socket part.

An example of this process is shown by the video available at Plastic and Reconstructive Surgery—Global Open: February 2020—Volume 8—Issue 2—p e2567, doi: 10.1097/GOX.0000000000002567 (incorporated by reference) which displays the 3D-printed training model being assembled together with trial of vessel clamp and the different orientation/angulation scenarios that can be created to adjust the level of complexity of microvascular anastomosis training process.

Anastomosis is the union of parts of blood vessels so as to intercommunicate or interconnect. Preferably, anastomosis training involves end-to-end or end-to-side connection of vessels. However, other procedures may be practiced using the device disclosed herein including inspection or dissection of vascular tissues having geometric characteristics such as variable cross-sectional shape, a variable cross-sectional area, a turn, a bend, a bifurcation, a junction, a convolution, an anastomosis, or combinations thereof or procedures involving surgical modification of such vascular tissues.

Vascular tissue. Vascular tissue comprising blood vessels for use in a training procedure may be obtained from animal tissue. Examples of vascular tissue containing blood vessels include chicken arteries or veins, for example, those in chicken wings, or vascular tissue from rats; see Kim, Byeong Jin et al. *An efficient microvascular anastomosis training model based on chicken wings and simple instruments*. Journal of cerebrovascular and endovascular neurosurgery vol. 15,1 (2013): 20-5. doi:10.7461/jcen.2013.15.1.20, or Pruthi, Nupur et al. *Establishing a Training Model for Side-to-Side Anastomosis using Rat Femoral Vessels: Immediate and Delayed Patency*. Asian journal of neurosurgery vol. 13,3 (2018): 590-594. doi: 10.4103/ajns.AJNS_201_16, both incorporated by reference. In some embodiments, vascular tissue ethically obtained from a human body, such as that from a cadaver may be used. A vascular tissue may also comprise, or be constructed from, biological materials comprising collagen scaffold, a biodegradable polymer; and vascular cells.

Artificial vascular tissue. Some embodiments of the disclosed training methods disclosed herein may be performed using synthetic or artificial vascular tissue or replicas of vascular tissue. Examples of synthetic vascular tissue include commercially available saphenous veins such as those available at hypertext transfer protocol secure://www.3-dmed.com/product/saphenous-veins/ (last accessed May 29, 2020).

Dimensions. The inner and outer diameters, wall thickness, and lengths of vascular or artificial vascular tissues may be selected based on the type of anastomosis training and on the skill level of the trainee. In some embodiments the natural or artificial vessels may have inner diameters ranging from about 0.5, 1, 2, 3, 4, 5, 6, 7, 8, 9 to about 10 mm, outer diameters ranging from about 1, 2, 3, 4, 5, 6, 7, 8, 9, 10, 11, 12, 13, 14, 15 to about 16 mm, a wall thickness ranging from about 0.25, 0.5, 0.75 to 1.0 mm, and lengths ranging from about, 4, 5, 6, 7, 8, 9, 10, 11, 12, 13, 14, 15 to about 16 cm. The length of the vascular tissue may adjusted by trimming prior to use in a training procedure. Preferably, the three dimensional parameters of the printed model file are adjusted prior to 3D printing to provide a device adapted to a particular training procedure or training materials such as vessels having different sizes.

3D printers. A 3D printer may be selected by one skilled in the art. Preferably, for convenience, a desktop 3D printer may be used. Examples of suitable printers include those produced by ULTIMAKER®. Further description of 3D printers and printing products is available and incorporated by reference to, hypertext transfer protocol secure://en.wikipedia.org/wiki/Ultimaker. In a preferred embodiment the device is produced via a 3D printing technique known as fused deposition modelling.

3D printing materials or inks. Those skilled in the art may select a suitable 3D printing material for printing of the training device disclosed herein. Such a printing material preferably may comprise, consist essentially of, or consist of one that prints a device that has chemical resistance and has flexibility and/or durability of rubber or plastic. A flexible thermoplastic polyurethane (e.g., TPU 95A) is preferred. Other printing materials may comprise, consist essentially of or consist of ABS, polycarbonate, polystyrene, acrylates, amorphous polyamides, polyesters, PPS, PPE, PEEK, PEAK, or mixtures thereof.

Figure 1A:
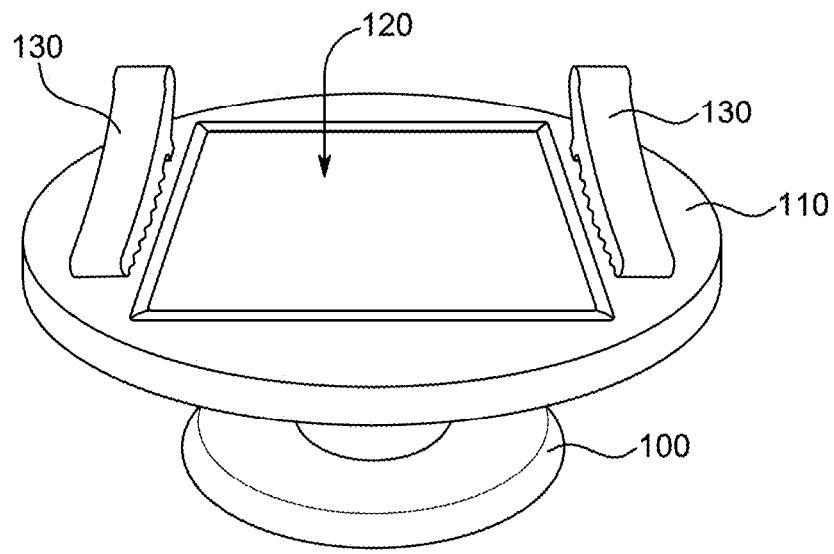
FIG. 1A. Frontal view of training tool comprising a base 100, a platform 110, a stage or work area 120 and clamps 130.
Figure 1B:
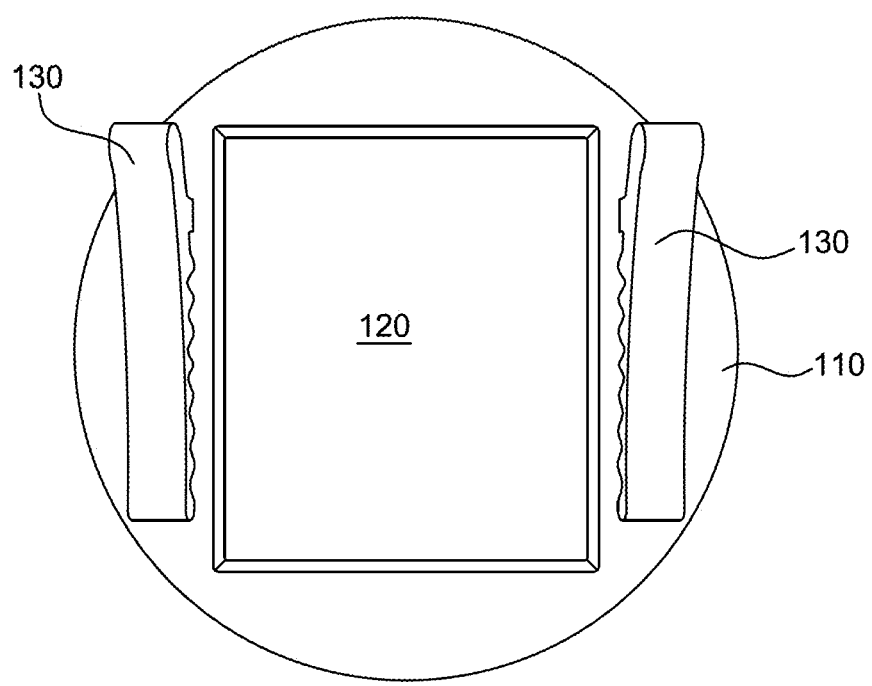
FIG. 1B. Top view of training tool showing platform 110, stage or work area 120 and clamps 130.
Figure 1C:
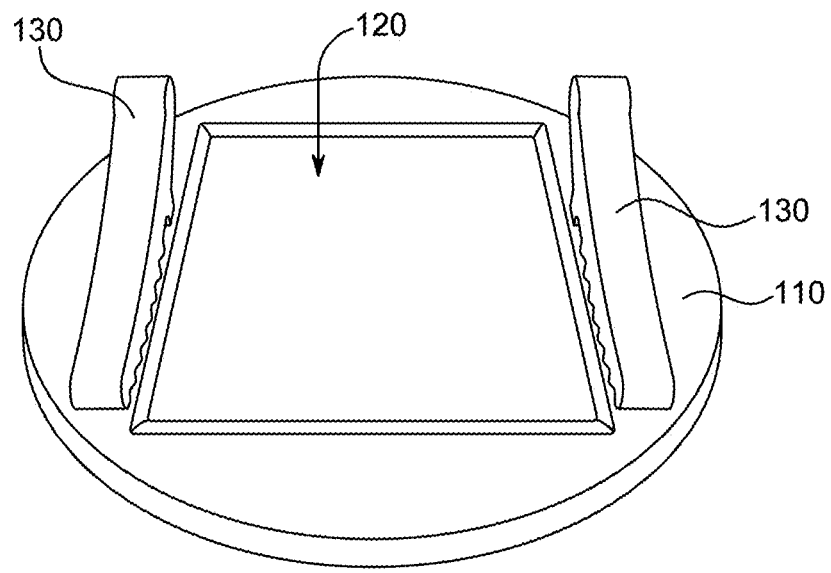
FIG. 1C. Frontal view of an embodiment of the training tool having a recessed stage or work area 120.
Figure 1D:
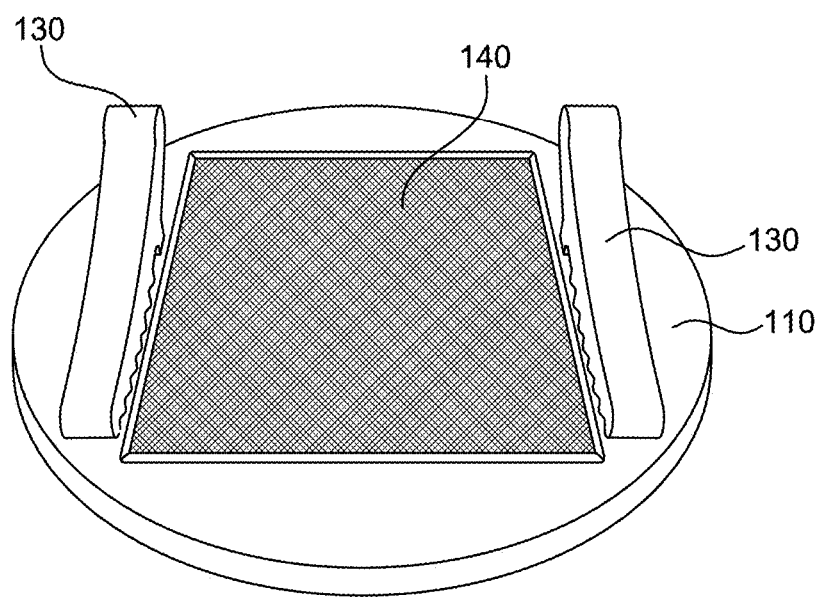
FIG. 1D. Frontal view of an embodiment of the training tool having a textured stage or work area 140.
Figure 1E:
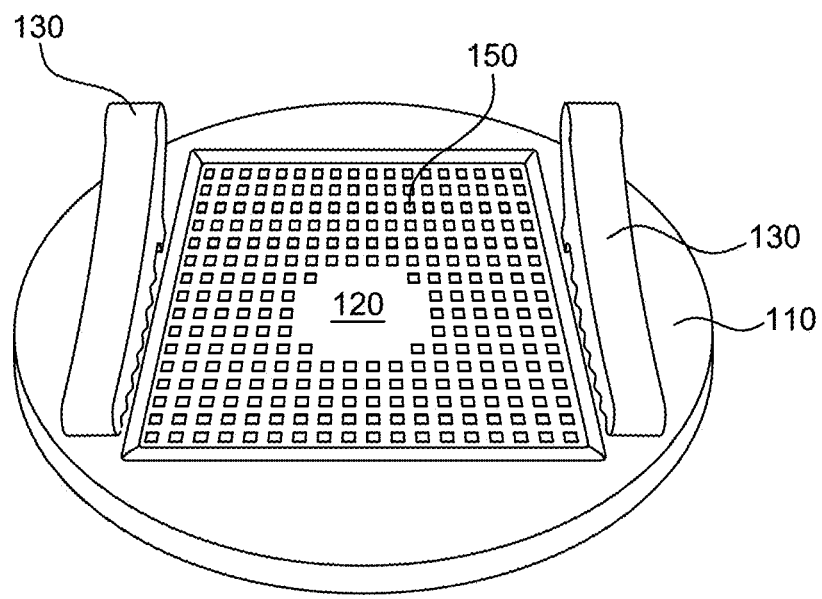
FIG. 1E. Frontal view of an embodiment of the training tool having a platform 120 comprising a grid 150.
Figure 1F:
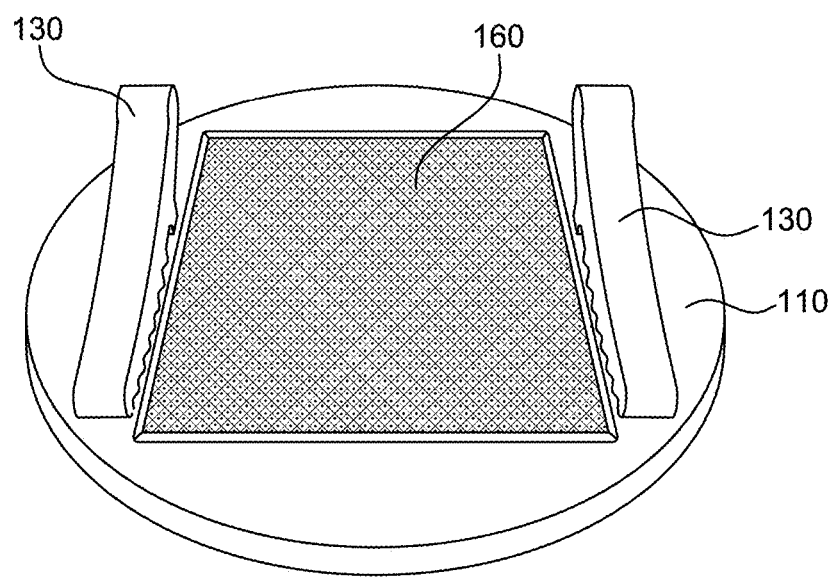
FIG. 1F. Frontal view of an embodiment of the training tool having a stage with a surface mesh 160.
Figure 1G:
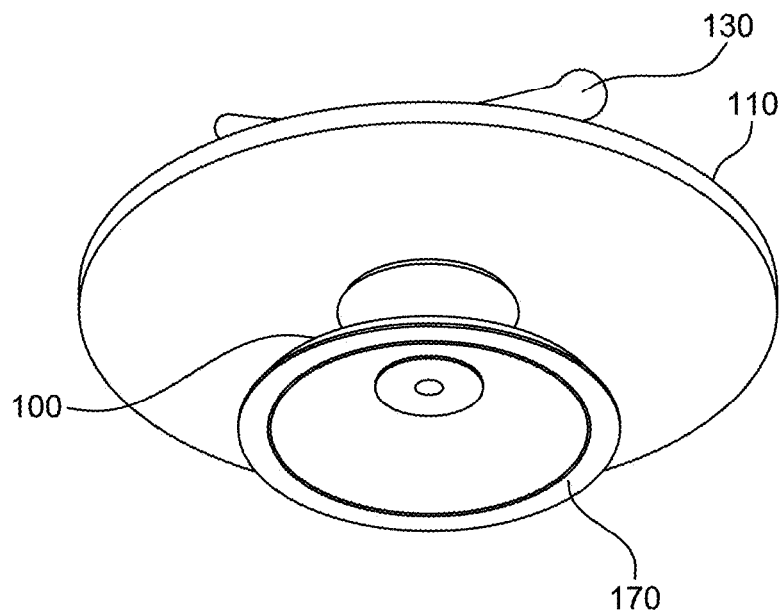
FIG. 1G provides a bottom view of an embodiment of one embodiment of the base 100, footing 170, stage 110 and clamp 130 of the training tool.
Figure 2A:
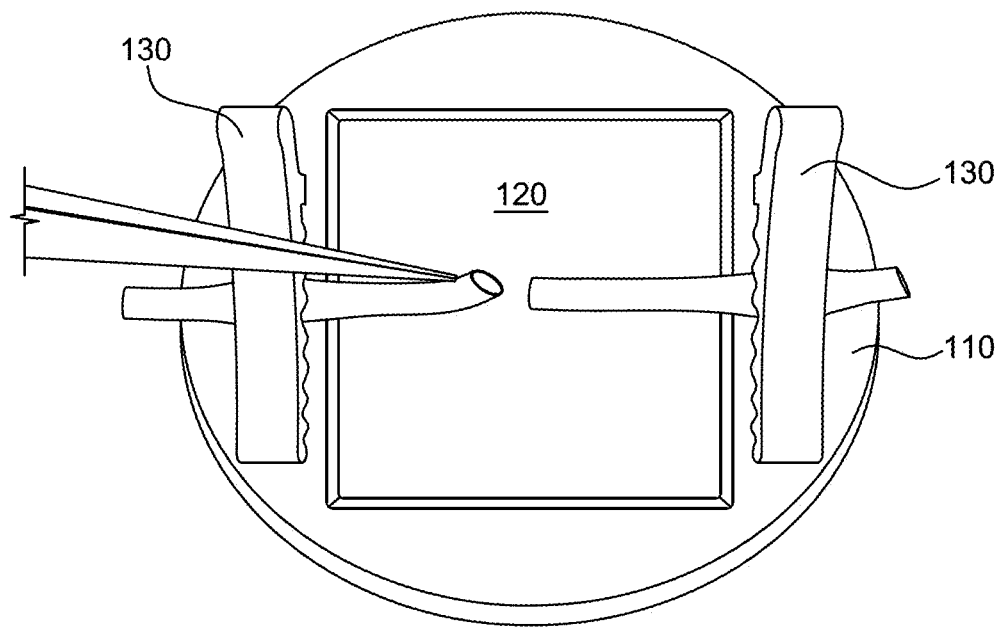
FIG. 2A depicts placement of two segments of vascular tissue on the stage 120 between the two clamps 130 for subsequent anastomosis practice.
Figure 2B:
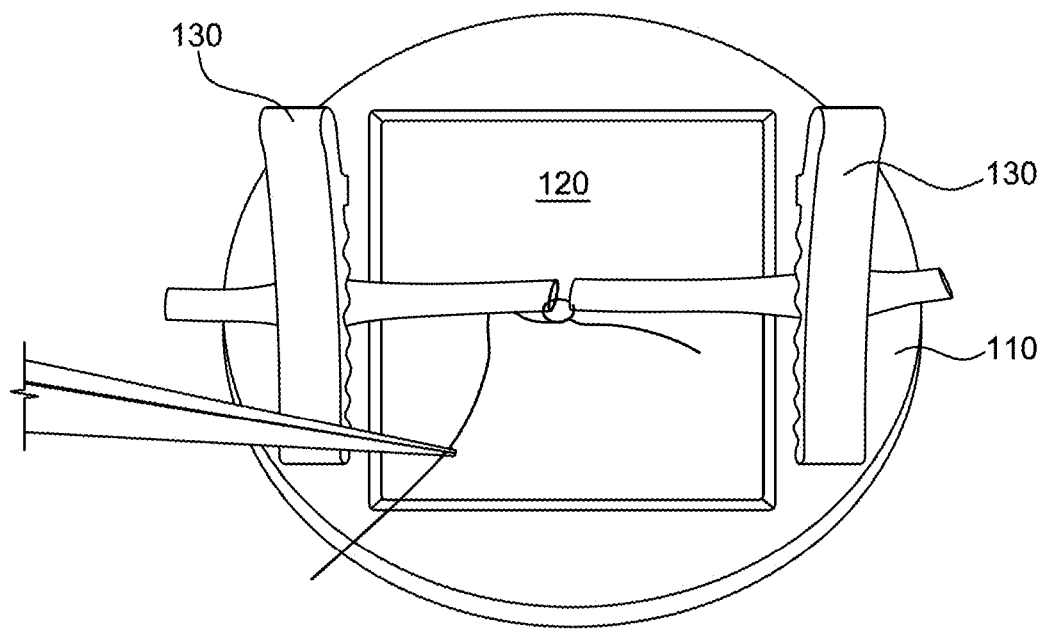
FIGS. 2B-2F depicts stages of anastomosis by suturing of vascular tissue secured on the stage 120 between the two clamps 130.
Figure 2C:
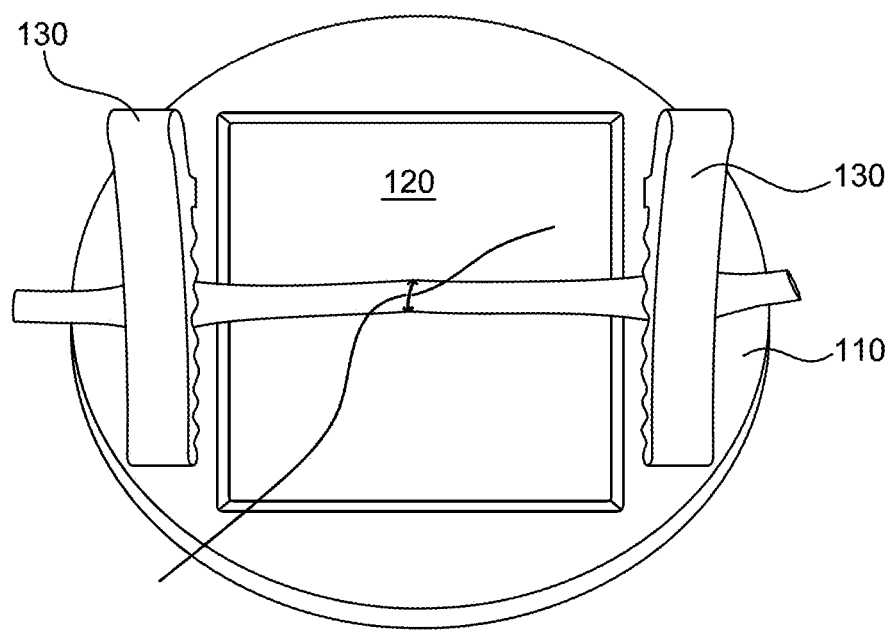
Figure 2D:
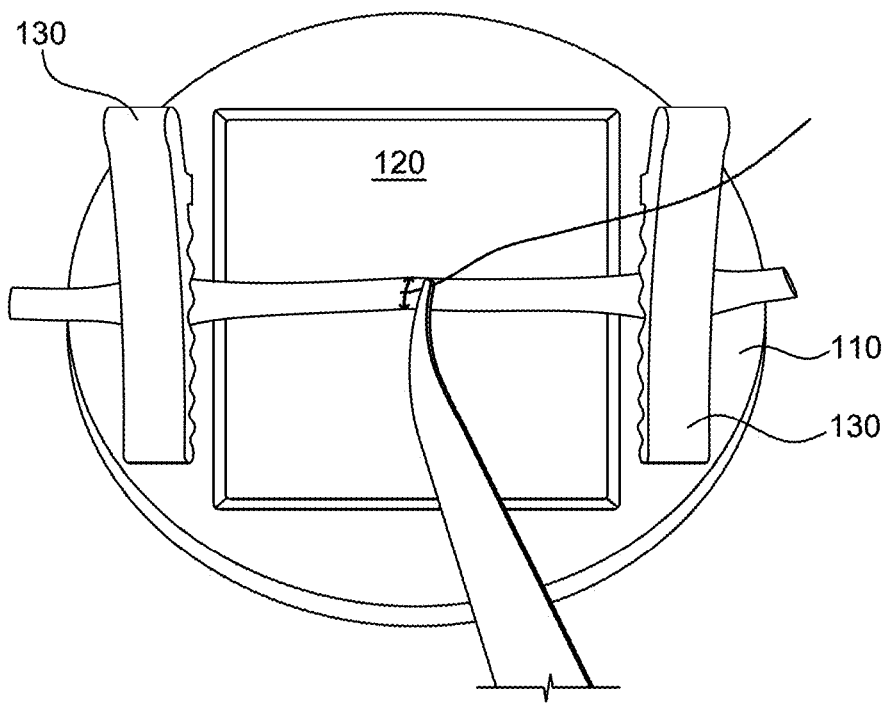
Figure 2E:
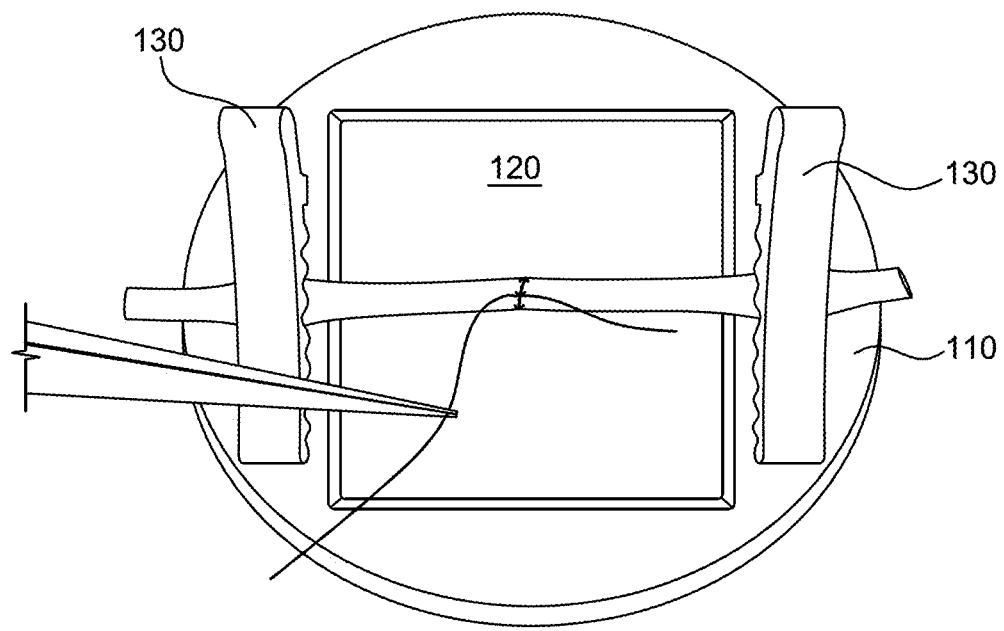
Figure 2F:
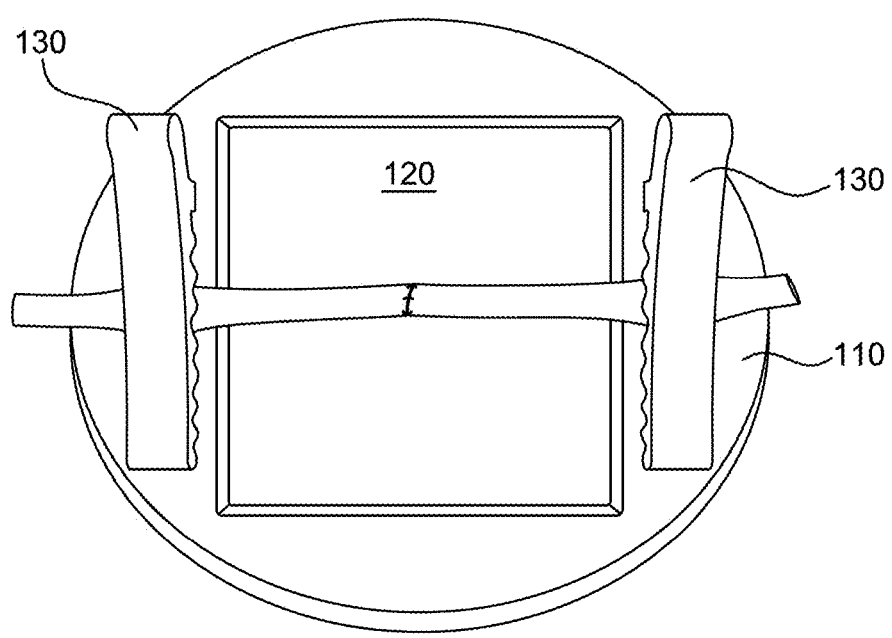
Figure 3A:
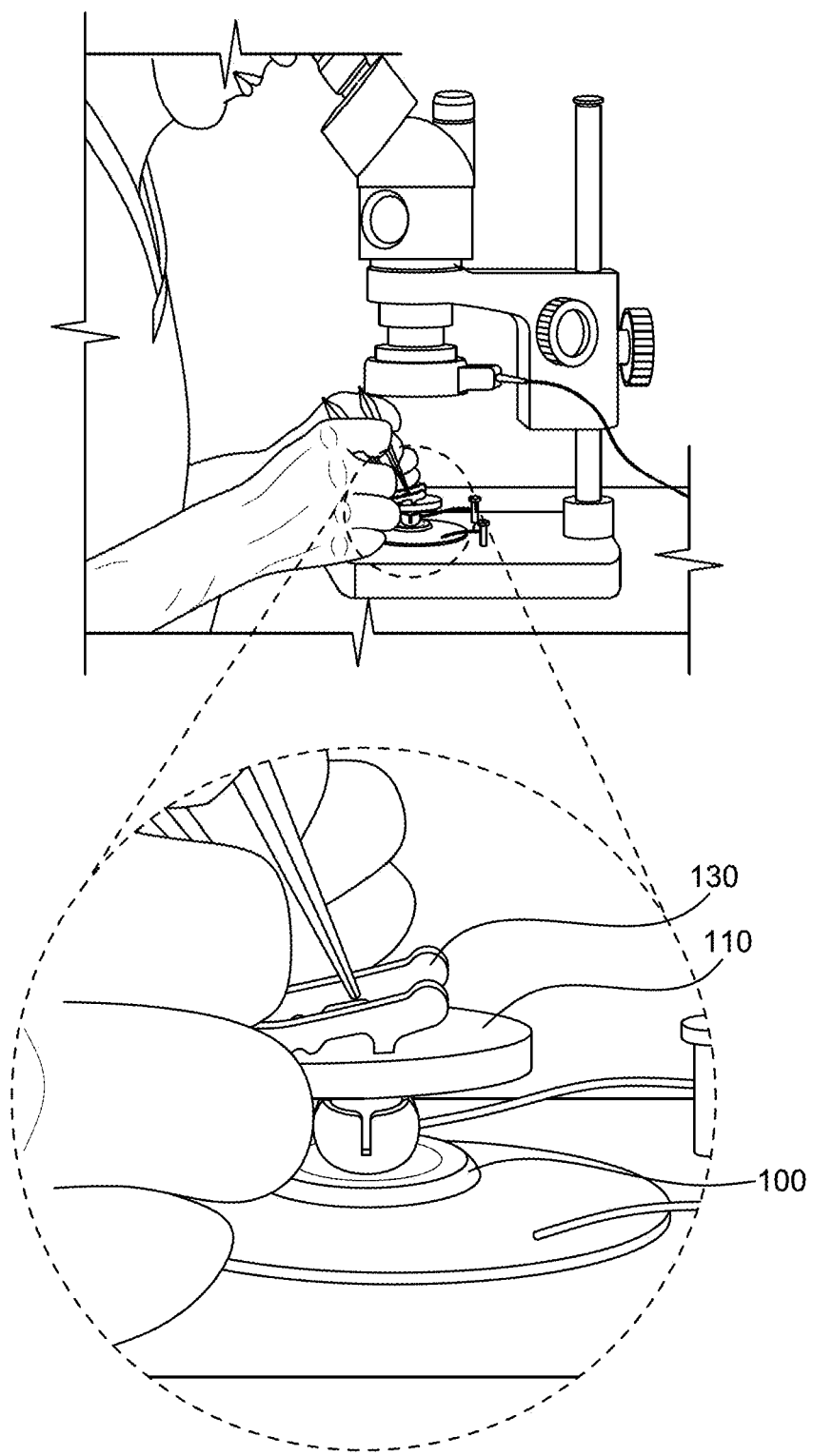
FIGS. 3A-3B depict positioning of the base of the training device on a microscope stage during practice anastomosis.
Figure 3B:
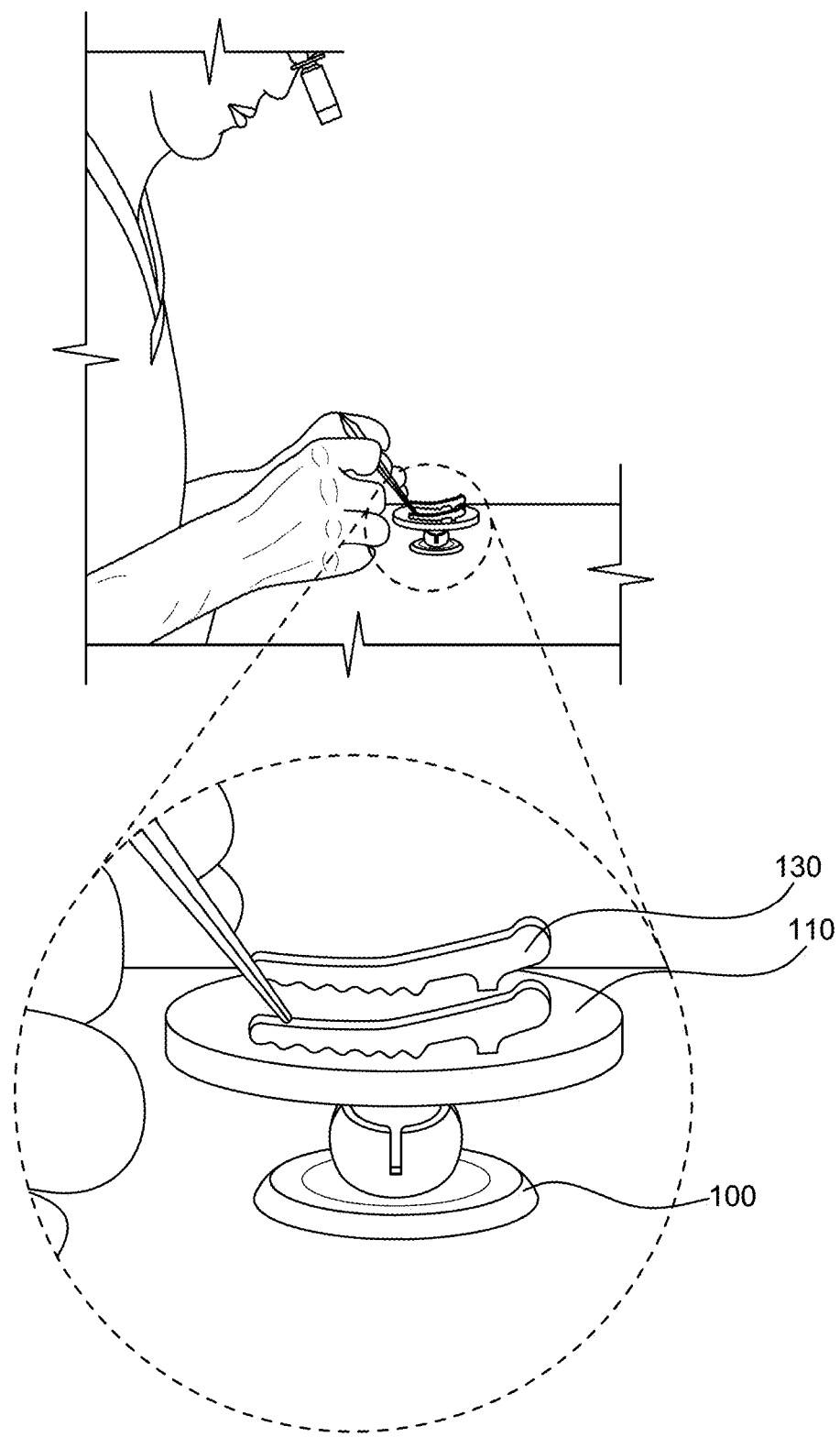
Figure 4A:
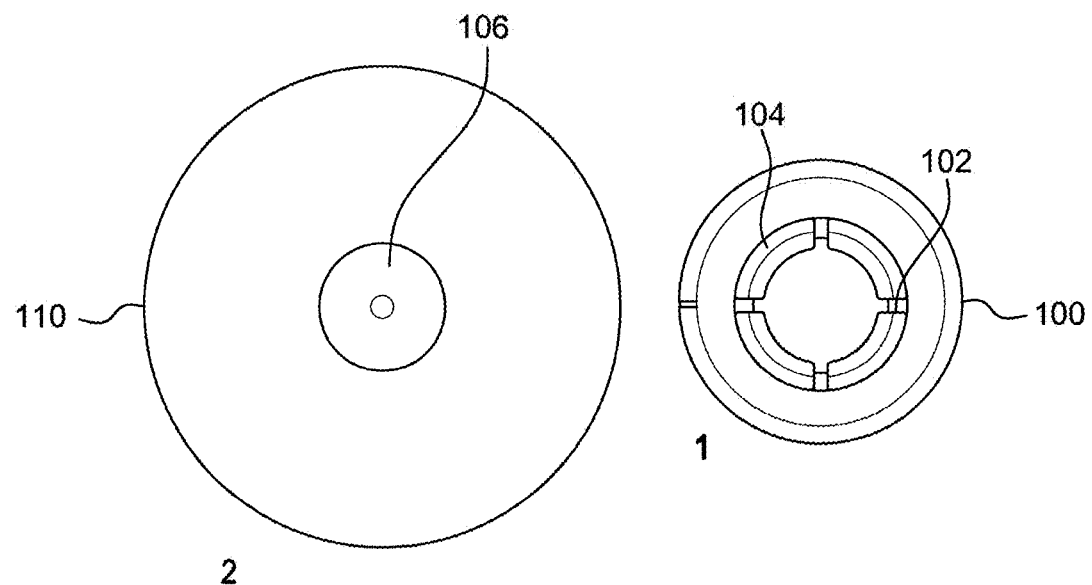
FIG. 4A provides a bottom view of the stage 110 and a rotatable ball 106 of a ball-in-socket joint which is attached to bottom part of stage 110 and which fits into a grooved 102 socket 104 which is attached to base 100. Reference characters 1 and 2 respectively refer to the bottom and top parts of the device.
Figure 4B:
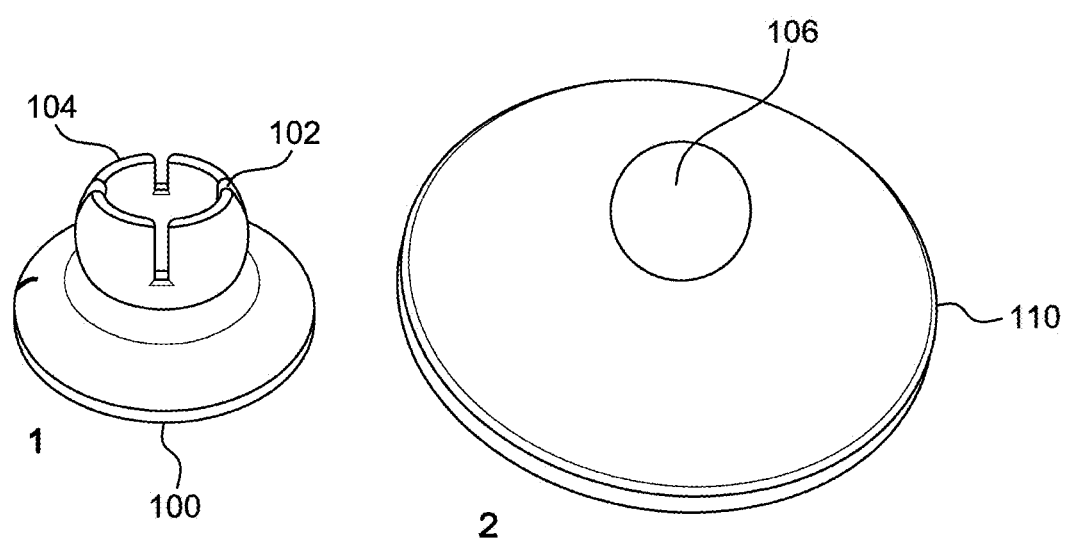
FIG. 4B provides a top side view of the stage 110 and a rotatable ball 106 of a ball-in-socket joint which is attached to bottom part of stage 110 and which fits into a grooved 102 socket 104 which is attached to base 100. Reference characters 1 and 2 respectively refer to the bottom and top parts of the device.
Figure 4C:
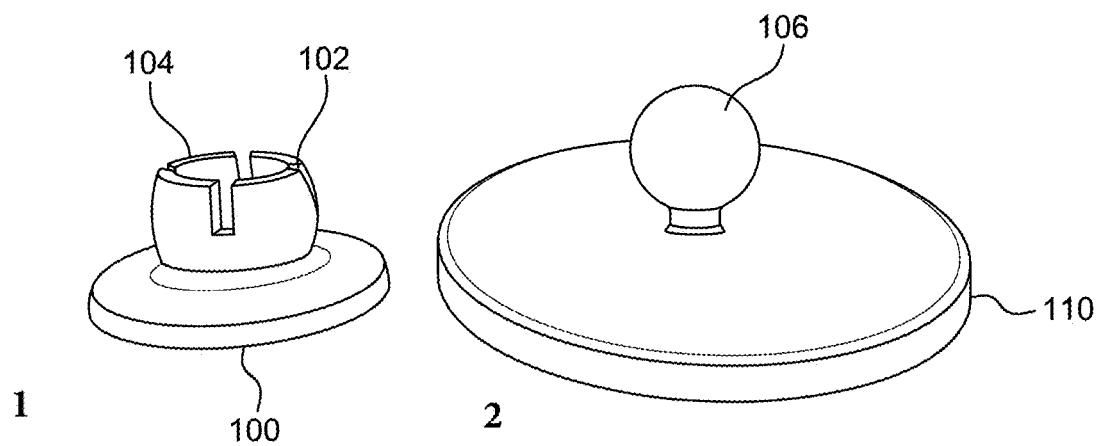
FIG. 4C provides a side view of the stage 110 and a rotatable ball 106 of a ball-in-socket joint which is attached to bottom part of stage 110 and which fits into a grooved 102 socket 104 which is attached to base 100. Reference characters 1 and 2 respectively refer to the bottom and top parts of the device.
Figure 5A:
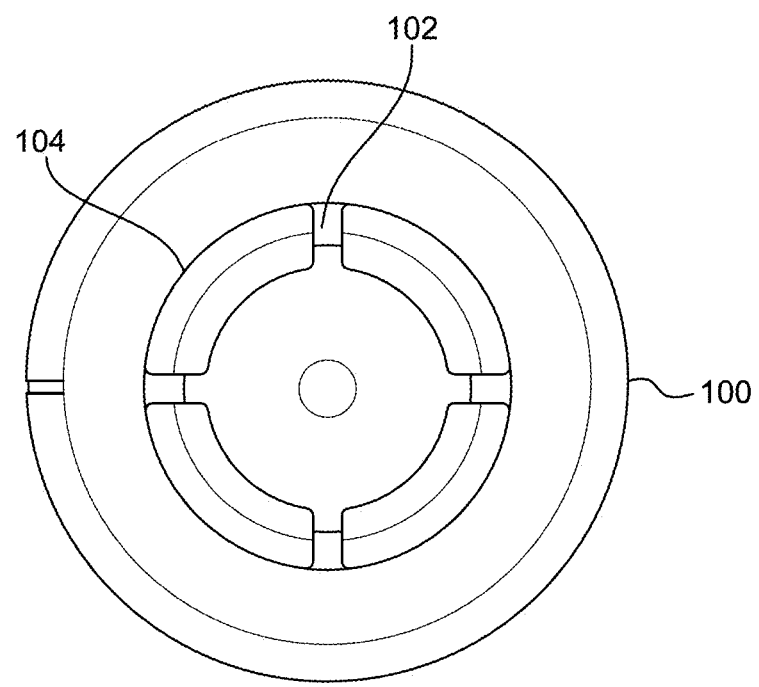
FIG. 5A represents a top view of the base 100 and grooved 102 socket joint 104.
Figure 5B:
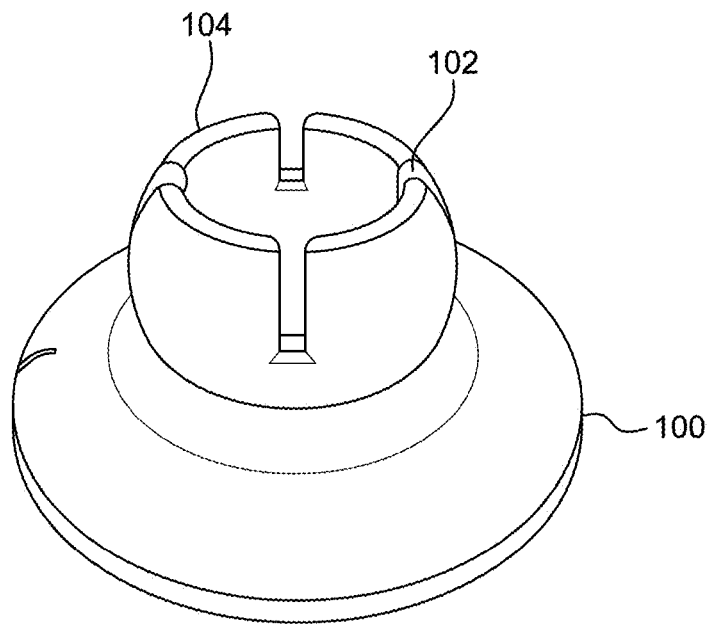
FIG. 5B represents a top side view of the base 100 and grooved 102 socket joint 104.
Figure 5C:
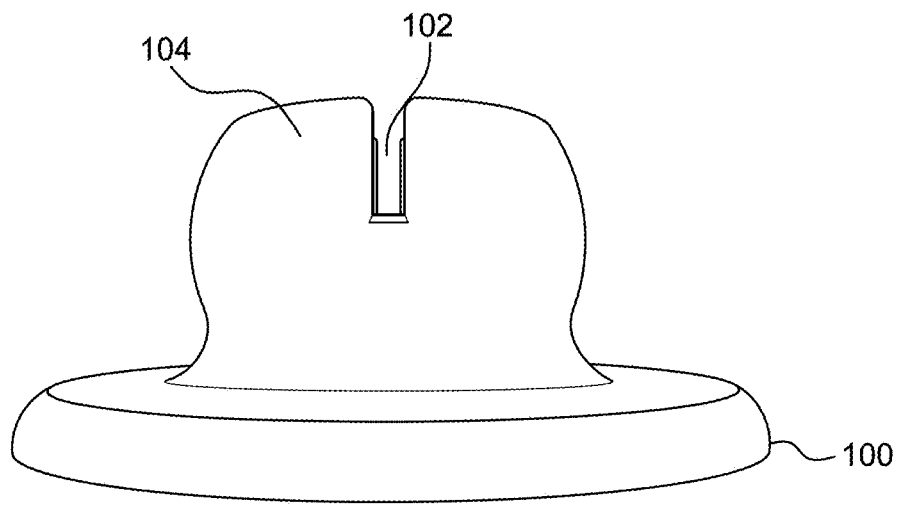
FIG. 5C represents a side view of the base 100 and grooved 102 socket joint 104.
Figure 6A:
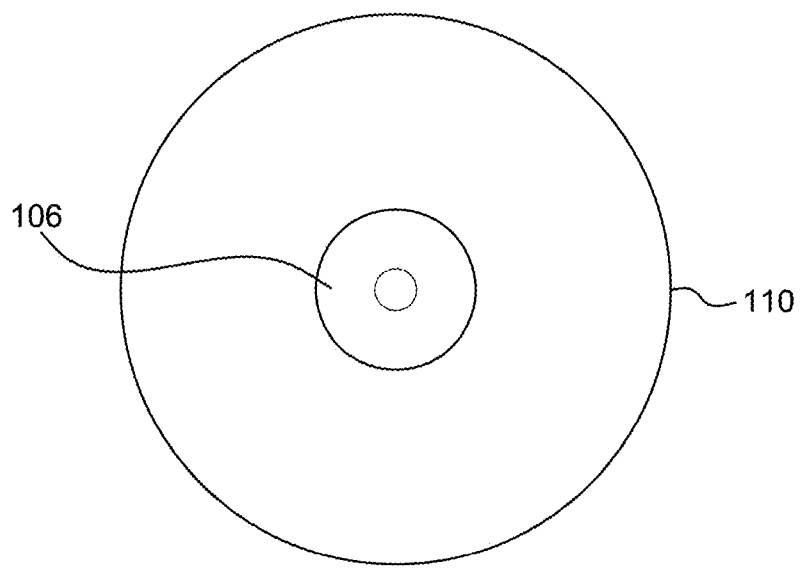
FIG. 6A shows a bottom view of the platform 110 and ball 106 of the ball-in-socket joint.
Figure 6B:
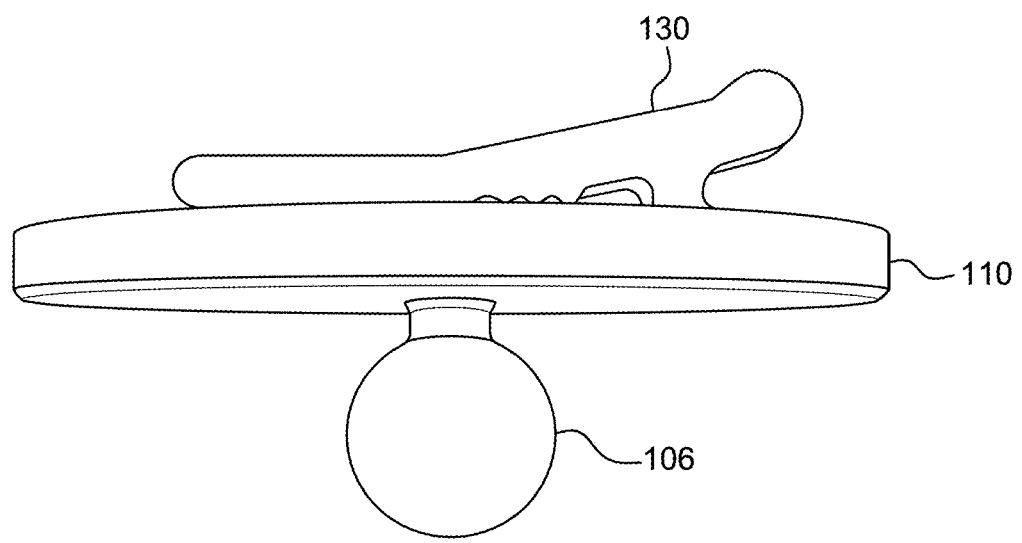
FIG. 6B shows a side view of the platform 110 and ball 106 of the ball-in-socket joint.
Figure 6C:
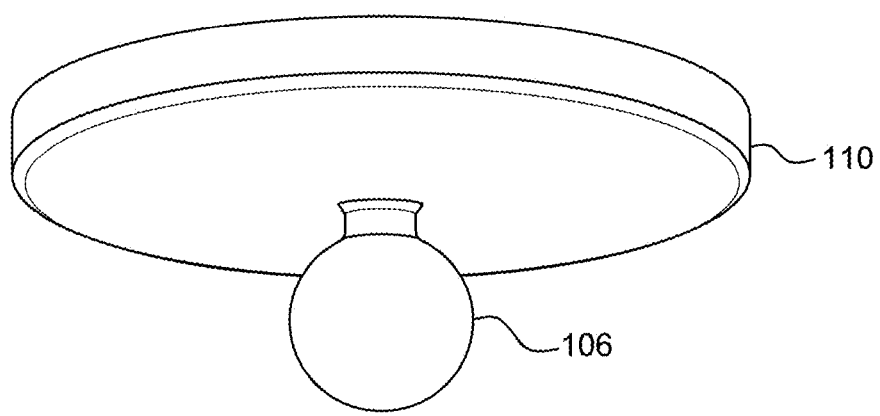
FIG. 6C shows a bottom side view of the platform 110 and ball 106 of the ball-in-socket joint.
Figure 7A:
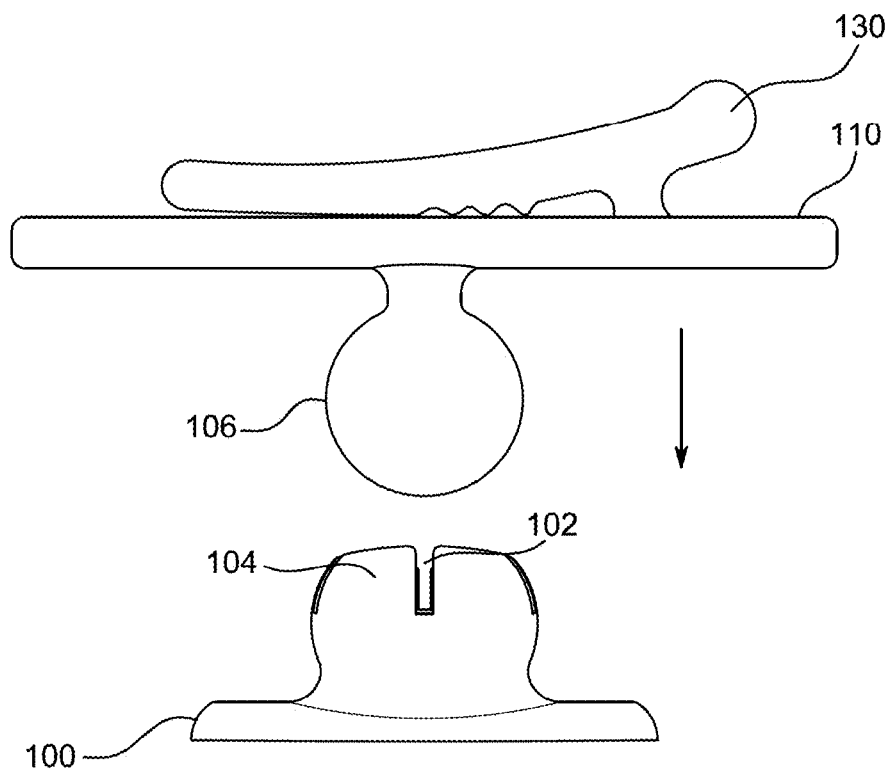
FIG. 7A shows a side view of the upper part of the device comprising a platform 110 and clamp 130 positioned over a lower part of the device comprise base 100 and grooved 102 socket 104.
Figure 7B:
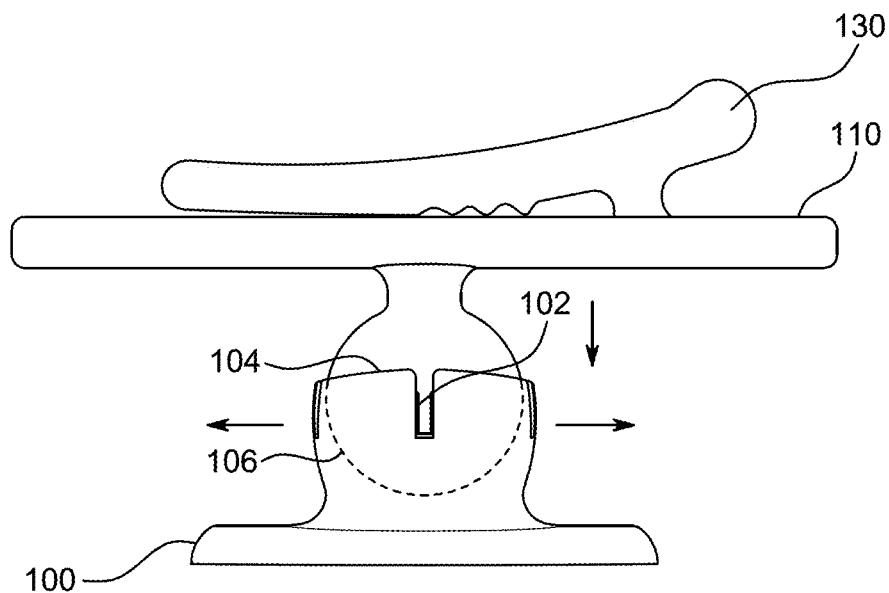
FIG. 7B-7C depict how the two parts of the device connect via an adjustable ball-in-socket joint which comprises ball 106 and grooved 102 socket 104.
Figure 7C:
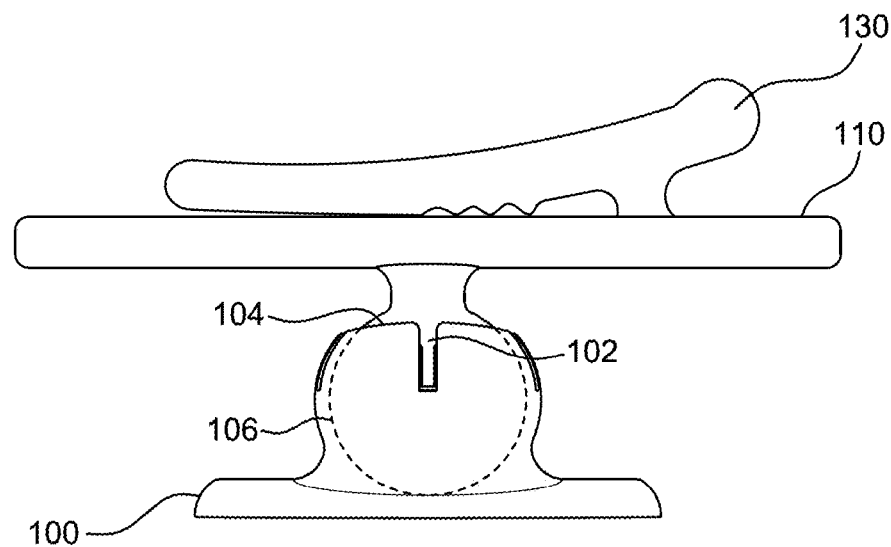
Figure 8A:
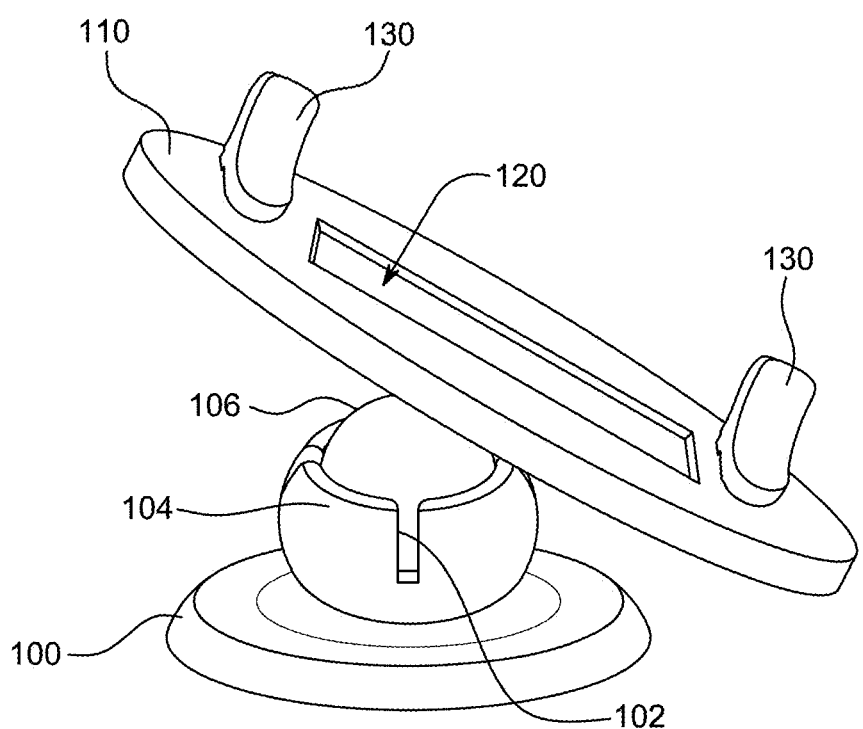
FIGS. 8A-8C show how the position of the stage or working area 120 can be tilted or rotated using the ball joint. Other characters: base 100, socket 104, vertical gap or window in socket 102, ball portion of upper unit 106.
Figure 8B:
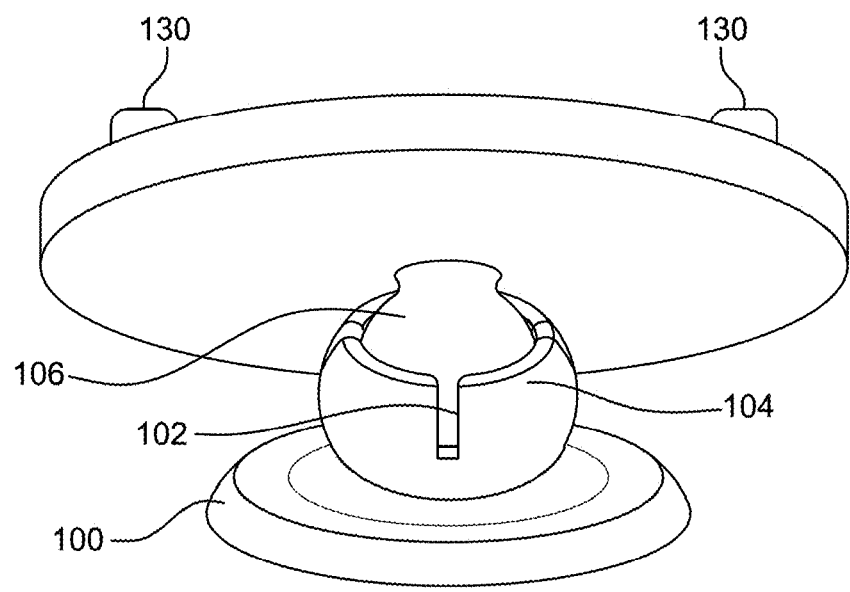
Figure 8C:
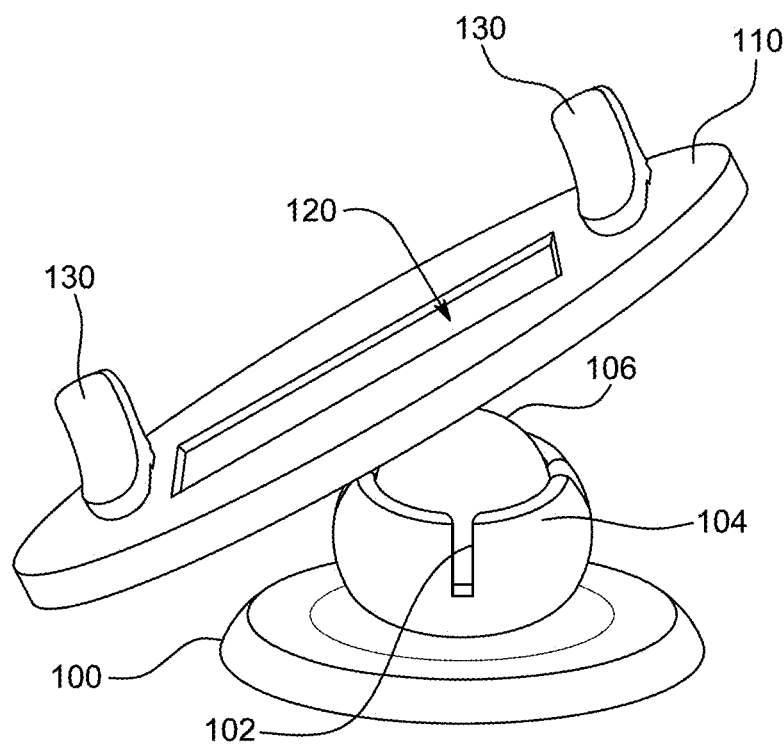
Figure 9:
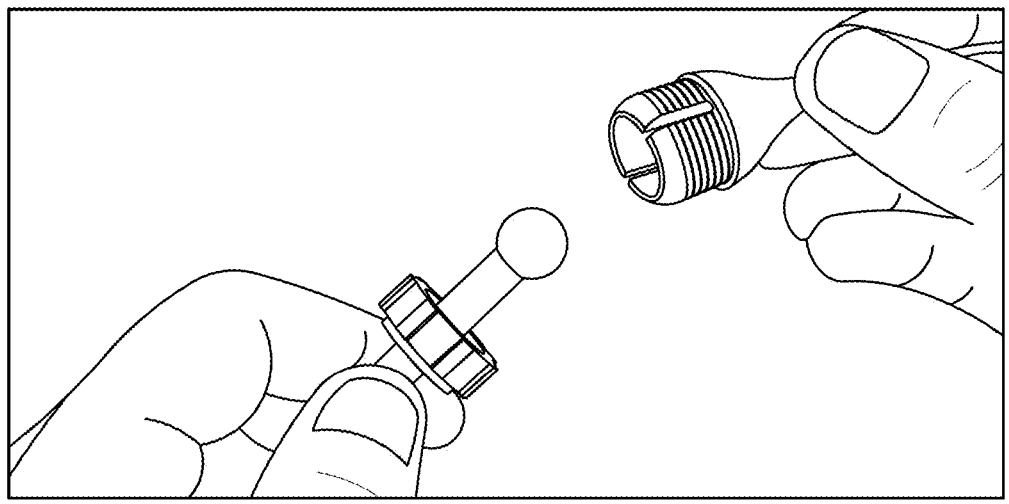
FIG. 9 depicts a locking ball-in-socket joint.

3D printing and assembly. Typically, the device disclosed herein is printed as two parts, the upper part comprising the stage and ball of the ball-in-socket joint, and a lower part comprising the base and the socket of the ball-in-socket joint. These two pieces can be assembled as described by FIGS. 7A-7C.

Platform. The platform has a thickness selected to provide stability and easy of movement by tilting or rotation, for example, it may range in thickness from about 0.5, 1.0, 1.5 to 2 cm. The size and shape of the platform may be selected by those skilled in the surgical or medical training fields. Typically, the platform is round, which provides for its easy rotation to provide different angles of accessibility of vascular tissues clamped to it. In some embodiments, it may be oval, rectangular or square or other shape adapted to its use for training for a particular type of anastomosis or other surgical procedure.

Vascular clamps (clips, attachments). One or more, preferably a pair of, vascular clamps suitable for securing vascular tissue to the stage of the device may be selected by one skilled in the art. Vascular clamps are described by, and incorporated by reference to, U.S. Pat. Nos. 7,144,402 and 6,468,285; and to Ikuta, Y., *Microvascular Double Clamp Type A-II*, J. Reconstructive Microsurgery 1(1): 41-43 (July 1984), Yoshii, T., et al., *A New Disposable Microvascular Double Clip*, J. Reconstructive Microsurgery 3(2):133-136, Narayanan, K et al., *A New Variable Pressure Microvascular Clamp*, Microsurgery 9(1):52-54 (1988), and to Smahel, J., et al., *New Disposable Microvascular Clamp*, Microsurgery 6(2):129-131 (1985). In some embodiments, the vascular clamps are pinned or glued to the surface of the platform. Preferably the vascular clamps are formed integrally with the device so as to permit a flush platform portion plane. In other embodiments the clamp includes an elevated base portion that is elevated 0.5 mm, 1 mm, 1.5 mm, 2 mm, 3 mm, 5 mm, 10 or >10 mm above the plane of the platform portion. The elevated base portion preferably has width matching the width of the clamp but may alternately have a width that is 1.5×, 2×, 3×, or 5× the width of the clamp.

Ball-in-socket joint. In preferred embodiments, the lower portion of the device has four equally spaced grooves in the socket which help fit and secure the ball of the upper portion into the socket. In alternative embodiments, 0, 1, 2, 3, 4 or more than 4 grooves may be printed into the socket. In some embodiments, a lubricant may be placed on the surfaces of the ball-in-socket joint. In other embodiments, the socket comprises external threads compatible with threads on a screw on the upper unit so that the ball portion of the upper unit and the socket portion of the lower unit can be secured by tightening the cap on the external threads of the socket portion thereby securing the ball-in-socket joint or increasing its tightness.

The use of 3D printing permits customization of the dimensions of the device so as to adapt it to a particular training procedure or for use with particular types or sizes of vessels. In one embodiment, the diameter of the top platform is about 5 cm, the clamp length is about 2.8 cm, the ball width is about 1.2 cm and ball height about 1.5 cm, the working space on the platform is about 2.9×3.3 cm, the socket width is about 1.1 cm and socket height about 1 cm, the base diameter about 3 cm, the width of grooves is about 1 mm and the groove height is about 4 mm. In other embodiments, each of the above parameters may be modified, for example, by <5, 5, 10, 20, 30, 40, 50% or more.

In some embodiments, the ball further comprises a rod which joins it to the platform. The rod may further comprise a ball-in-socket type joint or other joint between lower part of the platform and the ball-in-socket joint attached to the base.

In some embodiments, the upper end of the socket into which the ball fits, is threaded and a rod which attaches the ball to the lower surface of the platform on one end and comprises the ball fit to the socket on the other end has a screwcap or attachment that can secure the ball into the socket and prevent the ball from being separated from the socket. In some embodiments, the cap can be tightened so as to tighten the fit between the ball and the socket or to secure the ball into a fixed position in the socket.

In another embodiment, the surface of the ball has ridges or indentations which interact with inner surface ridges or indentations in the socket. These interactions help control the rotation and tilt angulation of the platform.

In one embodiment, the fit, motion and tilt control of the device is guided by the elasticity of the socket material into which the ball fits. This elasticity permits the socket stretch slightly to move the ball and control its motion.

Base. The lower portion of the device comprises a base which is connected to the socket. The base provides a stable footing for the device and is typically about 4-12 cm in diameter and about 0.25 to 2 cm thick. In some embodiments, a surface of the base is attached to an substrate, such as an operating table, desk, or microscope platform, for example by a mechanical fastener, clips, or by an adhesive, such as with adhesive tape to secure the device during a training procedure such as anastomosis.

Training. The 3D printed device disclosed herein can be used for training in several fields including vascular surgery including anastomosis training, reconstructive microsurgery, neurosurgery, and ophthalmology. It can be used in a skill laboratory and for clinical simulations. It is inexpensive, has a compact size, is easy to assemble and use, minimizes the use of animals for training purposes and associated ethical concerns, and permits training in multiple scenarios of microsurgery involving complex angulation and orientations. Use of the device will permit development and increases in the skill of microsurgeons in training and will thus provide improved clinical outcomes and a corresponding reduction in microsurgery risks.

Training system. A training system may comprise the device as disclosed herein as well as a microscope, such as a binocular microscope, lights, anastomosis training cards, samples of natural vascular or artificial vascular tissue, as well as instructions for use in practicing anastomosis.

EXAMPLE

A training prototype was designed using CAD software (Rhino3D) and then 3D-printed with a thermoplastic polyurethane (TPU 95A) semi-flexible filament using a desktop 3D printer (ULTIMAKER® 2) which uses a fused deposition process. The printed training tool was assembled by fitting the ball-and-socket mechanism between two parts having an overall round table top (platform) with integrated vascular clamps; see the video available at Plastic and Reconstructive Surgery—Global Open: February 2020—Volume 8—Issue 2—p e2567, doi: 10.1097/GOX.0000000000002567 (incorporated by reference).

Trials with synthetic and nonliving animal blood vessels showed the utility of the clamps in holding the vessels within the working space. By rotating the top part, a multiaxial vessel orientation from 0 to 360 degrees with respect to the position of the trainee was achieved. The top part was also capable of multiangular orientation of the vessels (±30 degrees) regardless of its axial orientation during vessel anastomosis. For the 3D-printing process, the average printing time was about 3.5 hours with a material cost of $1.3 per device.

Trials with synthetic and nonliving animal blood vessels showed operability and functionality of the clamps for holding the detached vessels within the working space on the platform. By rotating the platform, a multiaxial vessel orientation between 0 and 360 degrees was achieved and the top unit was also capable of multiangular (tilt) orientation of the vessels by up to about 30 degrees during the vessel anastomosis. The trial showed the 3D-printed training device could be easily assembled and used with many different orientation/angulation scenarios which can adjust the level of complexity of microvascular anastomosis training.

As shown by these results, desktop 3D printing provides a convenient and inexpensive way to produce a microsurgical training device that permits scenarios with different levels of complexity because it provides trainees with an ability to train using various multiaxial and multiangular vessel orientations during the anastomosis.

The invention claimed is:

1. An anastomosis training device, comprising:
   an upper unit comprising
   a circular platform and two clamps, wherein the two clamps are disposed on opposite sides of the circular platform, and wherein each of the clamps is configured to hold a peripheral end of a vessel and hold the medial ends of the vessel in proximity so as to permit anastomosis of the medial ends, and
   a ball portion of a ball-in-socket joint; and
   a lower unit comprising a base and a socket portion of the ball-in-socket joint;
   wherein the upper and lower units are joined by connection of the ball portion of the upper unit and the socket portion of the lower unit; and
   wherein the ball portion of the upper unit comprises a threaded cap and the socket portion of the lower unit comprises external threads compatible with those on the threaded cap, wherein the cap fits over the ball portion and secures it to the socket.
2. The device of claim 1, wherein the upper and lower units are 3D printed.
3. The device of claim 1, wherein the upper and lower units are 3D printed with a material or ink comprising thermoplastic polyurethane.
4. The device of claim 1, wherein the upper and lower units are 3D printed with a material or ink comprising thermoplastic polyurethane semiflexible filament measuring 95A on the Shore durometer.
5. The device of claim 1, wherein the clamps on the upper unit are 3D printed and integral to the circular platform.
6. The device of claim 1, wherein the circular platform further comprises protractor markings around its circumference and wherein the base comprises a groove or mark for use as a reference point.
7. The device of claim 1, wherein the circular platform further comprises an inclinometer or tilt indicator that measures tilt in the X and Y directions.
8. The device of claim 1, wherein the ball portion of the upper unit is marked with protractor markings indicating a degree of tilt between 0 and 30 degrees along the X, Y or both X and Y axes.
9. The device of claim 1, wherein an upper surface of the circular platform is textured, comprises a surface coating to increase its coefficient of friction, and/or has surface fenestrations to allow fluid drainage.
10. A method for training a subject to perform anastomosis with the device of claim 1, the method comprising:
    clamping a peripheral end of a blood vessel to each clamp so that the medial ends of the blood vessels extend toward each other near the center of the circular platform,
    rotating the circular platform to a predetermined angle with respect to the subject,
    tilting the platform to predetermined angles between 0 and 30 degrees with respect to tilt along the X and Y axes of the platform, and
    surgically manipulating the ends of the blood vessels to form an anastomosis between them.
11. The method of claim 10, wherein the vessels are obtained from an animal.
12. The method of claim 10, wherein the vessels are obtained from a human cadaver.
13. The method of claim 10, wherein the vessels are synthetic.
14. The method of claim 10, wherein the surgical manipulating comprises suturing and or gluing ends of the vessels together.
15. A method for 3D printing the device of claim 1, comprising:
    selecting design parameters for the upper and lower units of the device,
    incorporating the design into stereo-lithography file format,
    3D printing the upper and lower units of the device using a 3D printer and the stereo-lithography file,
    removing excess material from the 3D printed upper and lower units,
    fitting the ball portion of the upper unit into the socket portion of the lower unit, thereby producing the device.
16. The method of claim 15, wherein the design parameters of the upper and lower unit comprise a design for a threaded cap and externally threaded socket and wherein the cap may be independently 3D printed from the upper unit.
17. The method of claim 15, wherein the 3D printing is performed using material or ink comprising thermoplastic polyurethane.
18. The method of claim 15, wherein design of the platform of the upper unit comprises protractor markings around the circumference of the platform which are 3D printed into or on to the platform and the design of the base of the lower unit comprises a reference point marking which is printed into or onto the base.

19. The method of claim 15, wherein design of the ball of the upper unit comprises protractor markings indicating a degree of tilt in the X and/or Y directions of 0 to 30 degrees which are 3D printed into or on to different sides of the ball with a spacing of 90 degrees.

* * * * *